United States Patent
Campbell et al.

(10) Patent No.: US 9,636,481 B2
(45) Date of Patent: May 2, 2017

(54) STEERABLE CATHETER WITH BRAKE ASSEMBLY

(71) Applicant: Boston Scientific Scimed, Inc., Maple Grove, MN (US)

(72) Inventors: Andrew Campbell, Reading, MA (US); Paul Barner, Valencia, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 681 days.

(21) Appl. No.: 14/038,311

(22) Filed: Sep. 26, 2013

(65) Prior Publication Data
US 2014/0088497 A1 Mar. 27, 2014

Related U.S. Application Data

(60) Provisional application No. 61/706,307, filed on Sep. 27, 2012.

(51) Int. Cl.
*A61M 25/01* (2006.01)
*A61B 1/005* (2006.01)

(52) U.S. Cl.
CPC ....... *A61M 25/0136* (2013.01); *A61B 1/0051* (2013.01); *A61B 1/0052* (2013.01); *A61B 1/0057* (2013.01); *A61M 25/0105* (2013.01); *A61M 25/0133* (2013.01); *A61M 25/0147* (2013.01)

(58) Field of Classification Search
CPC ... A61B 1/0021; A61B 1/0052; A61B 1/0057; A61M 25/0147; A61M 25/0136; A61M 25/0133; A61M 25/0105
USPC .................................. 604/98.01, 528, 95.04
See application file for complete search history.

(56) References Cited

U.S. PATENT DOCUMENTS

| 4,461,282 | A | * | 7/1984 | Ouchi | F16D 51/22 600/148 |
| 5,014,685 | A | * | 5/1991 | Takahashi | A61B 1/0052 600/148 |
| 2006/0264819 | A1 | * | 11/2006 | Fischer | A61M 25/0136 604/95.04 |
| 2008/0188871 | A1 | | 8/2008 | Smith et al. | |
| 2009/0287188 | A1 | | 11/2009 | Golden et al. | |

* cited by examiner

*Primary Examiner* — Laura Bouchelle
*Assistant Examiner* — Anh Bui
(74) *Attorney, Agent, or Firm* — Bookoff McAndrews, PLLC

(57) ABSTRACT

A catheter includes a handle and an elongate member extending from the handle. The catheter may also include steering system coupled to the handle. The steering system may be configured to deflect at least a portion of the elongate member in at least one direction. The catheter may also include a locking mechanism configured to lock the portion of the elongate member in a deflected configuration, and a lever coupled to the handle. The lever may be configured to move from a first position to a second position to engage the locking mechanism. The lever may also be configured to be separably retained at least at one of the first position or the second position to prevent movement therebetween.

16 Claims, 8 Drawing Sheets

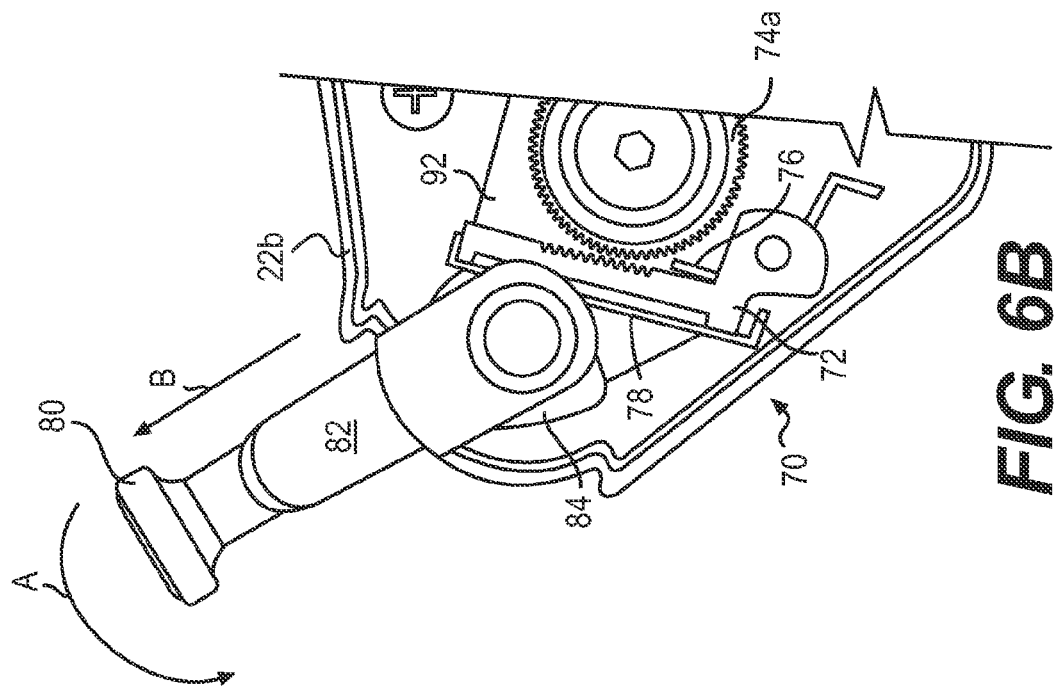
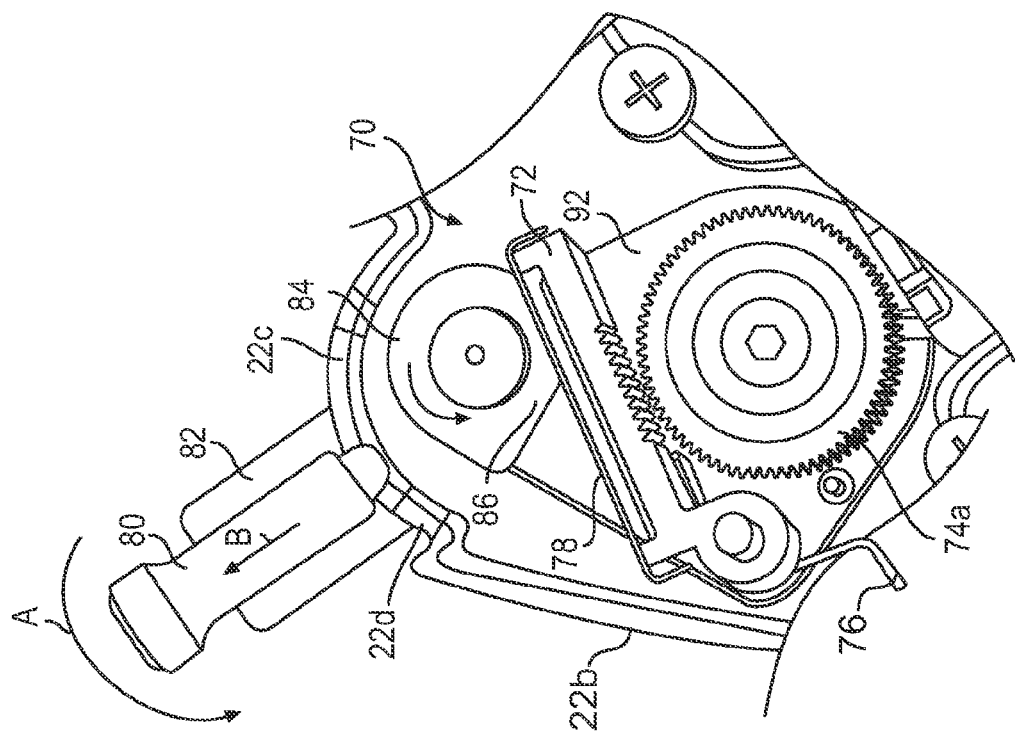

STEERABLE CATHETER WITH BRAKE ASSEMBLY

CROSS-REFERENCE TO RELATED APPLICATIONS

This application claims the benefit of priority from U.S. Provisional Application No. 61/706,307, filed Sep. 27, 2012, the entirety of which is incorporated by reference herein.

BACKGROUND OF THE INVENTION

Minimally invasive surgical tools, such as endoscopic and laparoscopic devices, provide access to areas or work sites within a mammalian body while minimizing patient trauma. These devices allow physicians to perform a variety of diagnostic and therapeutic tasks at a desired work site within the body by controlling the device from outside the body. In an exemplary procedure using such a device, the device is inserted into the body through a natural orifice or an incision, and positioned with its distal end proximate the work site. Surgical or diagnostic tools may then be delivered to the work site through the inserted device and controlled from outside the body to perform the desired task. While this task is performed, care must be taken to prevent inadvertent movement of the endoscopic device and its associated tools. The current disclosure relates to an endoscopic device with a braking assembly to prevent inadvertent movement of the device within the body.

SUMMARY OF THE INVENTION

In one embodiment, a catheter is disclosed. The catheter may include a handle and an elongate member extending from the handle. The catheter may also include steering system coupled to the handle. The steering system may be configured to deflect at least a portion of the elongate member in at least one direction. The catheter may also include a locking mechanism configured to lock the portion of the elongate member in a deflected configuration, and a lever coupled to the handle. The lever may be configured to move from a first position to a second position to engage the locking mechanism. The lever may also be configured to be separably retained at least at one of the first position or the second position to prevent movement therebetween.

Various embodiments of the invention may also include one or more of the following aspects: the locking mechanism may include a rack gear and at least one pinion gear that mate when the locking mechanism is engaged by the lever; the steering system may include at least one spool that is configured to rotate to deflect the portion of the elongate member, the at least one pinion gear may be coupled to the at least one spool such that relative rotation between them is prevented; movement of the lever from the first position to the second position may cause the rack gear to mate with the at least one pinion gear; the steering system may include two spools, each spool may be configured to deflect the portion of the elongate member in a different direction, wherein the rack gear prevents the rotation of both spools when the locking mechanism is engaged by the lever; the locking mechanism may include a cam that rotates to push the rack gear towards the at least one pinion gear when the lever moves from the first position to the second position; the locking mechanism may include a leaf spring configured to act as an interface between the cam and the rack gear; the locking mechanism may include a spring configured to bias the rack gear in a direction away from the at least one pinion gear; the locking mechanism may include a spring configured to bias the lever towards the handle, and the handle may include a retention feature configured to retain the lever at least at one of the first position or the second position; the retention feature may be an opening in the handle, and the lever may be separably retained by the handle by accommodating a distal end of the lever in the opening; and the lever may be configured to be pulled in a direction away from the handle and pivot relative to the handle to move from the first position to the second position.

In another embodiment, a catheter is disclosed. The catheter may include a handle, an elongate member extending from the handle, and a steering system with a locking mechanism. The steering system may include at least one spool configured to rotate to deflect at least a portion of the elongate member in at least one direction, a pinion gear fixedly coupled to the at least spool, and a rack gear configured to engage with the pinion gear to lock the portion of the elongate member in a deflected configuration.

Various embodiments of the invention may also include one or more of the following aspects: the steering system may include a cam configured to push the rack gear towards the pinion gear; the steering system may include a lever coupled to the handle and configured to move from a first position to a second position to engage the rack gear with the pinion gear; the lever may include a releasable lock that is configured to prevent movement of the lever between the first position and the second position; the releasable lock may include a spring that biases the lever towards a retention feature on the handle; and the steering system may include two spools, each spool may be fixedly coupled to a pinion gear, wherein each spool is configured to deflect the portion of the elongate member in a different direction.

In another embodiment, a method of using a catheter including a handle with an elongate member extending therefrom, is disclosed. The method may include positioning the catheter in a body with a distal end of the elongate member within the body and the handle outside the body, and activating a steering mechanism to deflect at least a portion of the elongate member in at least one direction. The method may also include engaging a locking mechanism of the catheter to lock the portion of the elongate member in a deflected configuration. Engaging the locking mechanism may include pulling a brake lever away from the handle to release a lock of the lever, and moving the lever from a first position to a second position.

Various embodiments of the invention may also include one or more of the following aspects: moving the lever may include rotating a cam to push a rack gear into engagement with a pinion gear fixedly coupled to a spool of the catheter; and the method may further include disengaging the locking mechanism by moving the lever from the second position to the first position.

BRIEF DESCRIPTION OF THE DRAWINGS

The accompanying drawings, which are incorporated in and constitute a part of this specification, illustrate exemplary embodiments of the invention and together with the description, serve to explain the principles of the invention.

FIGS. 6A and 6B illustrate portions of the steering system of the catheter of FIG. 1.

DETAILED DESCRIPTION

Disclosed herein are systems and methods for performing a medical task within a body by controlling devices and/or tools, inserted into the body, from outside the body. Although the current disclosure is generally applicable to any type of device inserted into the body to perform a diagnostic or a therapeutic task (such as, for example, endoscope, laparoscope, arthroscope, bronchoscope, colonoscope, cystoscope, enteroscope, hysteroscope, laryngoscope, mediastinoscope, sigmoidoscope, thoracoscope, catheter, sheath, etc.), for the sake of brevity, the inserted device is referred to herein as a steerable catheter. The catheter may be adapted for any type of access within the body (such as, for example, trans-oral, trans-anal, trans-vaginal, trans-urethral, trans-nasal, transluminal, laparoscopic, thorascopic, orthopedic, through the ear, and/or percutaneous access), and may be configured to perform any type of task (diagnostic, therapeutic, surgical, etc.) within the body. It is to be understood that both the foregoing general description and the following detailed description are exemplary only and are not restrictive of the invention, as claimed.

Figure 1:
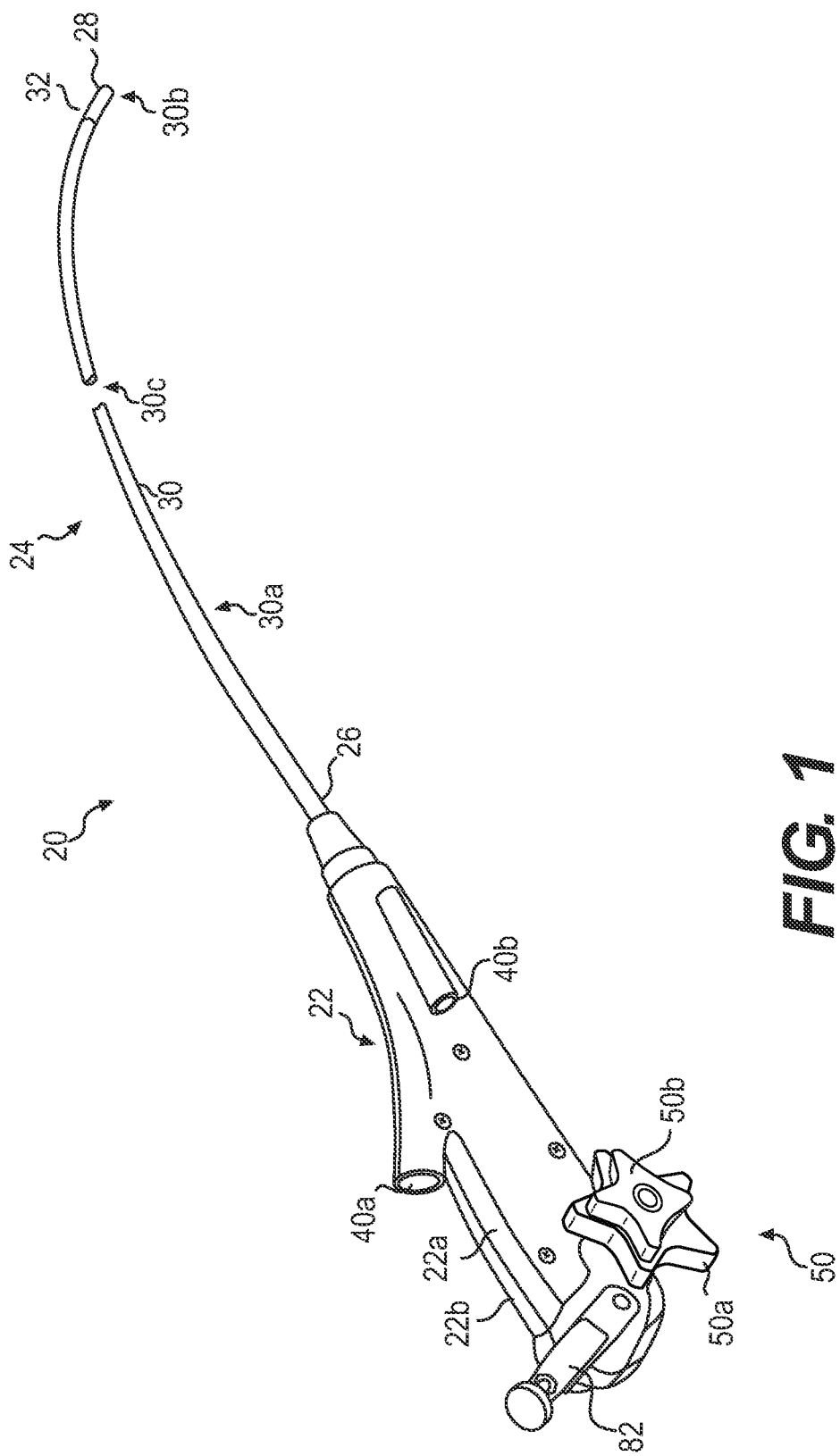
FIG. 1 is a perspective view of an exemplary steerable catheter of the current disclosure.

FIG. 1 is a perspective view of an exemplary embodiment of a steerable catheter 20 configured to perform a task within a mammalian body. Catheter 20 includes a handle 22 with an elongate member in the form of an insertion shaft or a guide tube 24 extending therefrom. In use, a distal end 28 of the guide tube 24 is inserted into the body and maneuvered to suitably position the distal end 28 proximate a work site within the body. In this configuration, the handle 22 is positioned outside the body with at least a portion of the guide tube 24 within the body. The handle 22 and the guide tube 24 may be made of any suitable material. Typically, the guide tube 24 is made of a biocompatible material such as, for example, nylon, polytetraflouroethylene (PTFE), polyethylene, thermoplastic elastomers, etc. Items, such as, for example, surgical or therapeutic tools, angioplasty balloons, stents, baskets, fiber optic scopes, light source, camera, etc. may be introduced to the work site within the body through the catheter 20. For instance, to introduce a surgical tool to the work site, the tool may be inserted into the catheter 20 through ports 40a, 40b on the handle 22, and pushed in to extend end effectors at the distal end of the tool out the distal end 28 of the guide tube 24. Actuation devices at the proximal end of the tools may be used by an operator of the catheter 20 (such as, for example, a surgeon) to manipulate the end effectors of the tools at the work site. In some embodiments, the catheter 20 may include, or engage with, a frame or another support device to support the handle 22 on a fixed object, such as an operating table frame.

Guide tube 24 includes an elongate body 30 that extends from a proximal end 26 to the distal end 28. The proximal end 26 of the guide tube 24 is coupled to the handle 22. The outer surface of elongate body 30 may include a layer of lubricous material to facilitate insertion of the guide tube 24 into the body. The interior of elongate body 30 may include one or more channels or lumens coupled to one or more of the ports 40a, 40b, and adapted to guide the tools to the work site. The number of lumens and their configuration may be varied depending on the intended use of the catheter 20 and the number and type of tools required during a procedure.

Elongate body 30 of guide tube 24 includes a proximal portion 30a, a mid portion 30c and a distal portion 30b. One or more of these portions may be flexible and configured to flex to allow the guide tube 26 to pass through tortuous passages within the body. One or more of these portions 30a, 30b, 30c may also include an articulation portion 32 (shown, for example, near the distal portion 30b in FIG. 1) configured to flex or bend by a desired amount in a desired direction in response to actuation by the surgeon. The articulation portion 32 may provide the guide tube 24 with multiple degrees of freedom. Catheter 20 includes a steering system 50 that may be activated by the surgeon to control the flexure or deflection of the articulation portion 32 and navigate the guide tube 24 through body lumens and/or point the distal end towards a desired work site. In some embodiments, the steering system 50 may include controls that may move the articulation portion 32 along different degrees of freedom. For example, in an exemplary embodiment, the steering system 50 includes a first dial (or knob) 50a that may be rotated to move the articulation portion 32 up and down, and a second dial 50b that may be rotated to move the articulation portion 32 left and right (or side to side). In some embodiments, the steering system 50 may also include controls that are configured to rotate at least a portion of the guide tube 24 about an axis of the guide tube 24. Although the guide tube 24 is described as being configured to deflect or flex at articulation portion 32, this is only exemplary. In some embodiments, guide tube 24 may include multiple flexible sections (such as, multiple articulation portions 32) arranged along the length of elongate body 30. Some of these multiple articulation portions may be configured to flex independently in response to activation by the surgeon. Activation of these multiple articulation portions 32 may enable the guide tube 24 to bend in complex shapes (such as, for example, s-shape) in one or more planes and/or about one or more axes.

Figure 2:
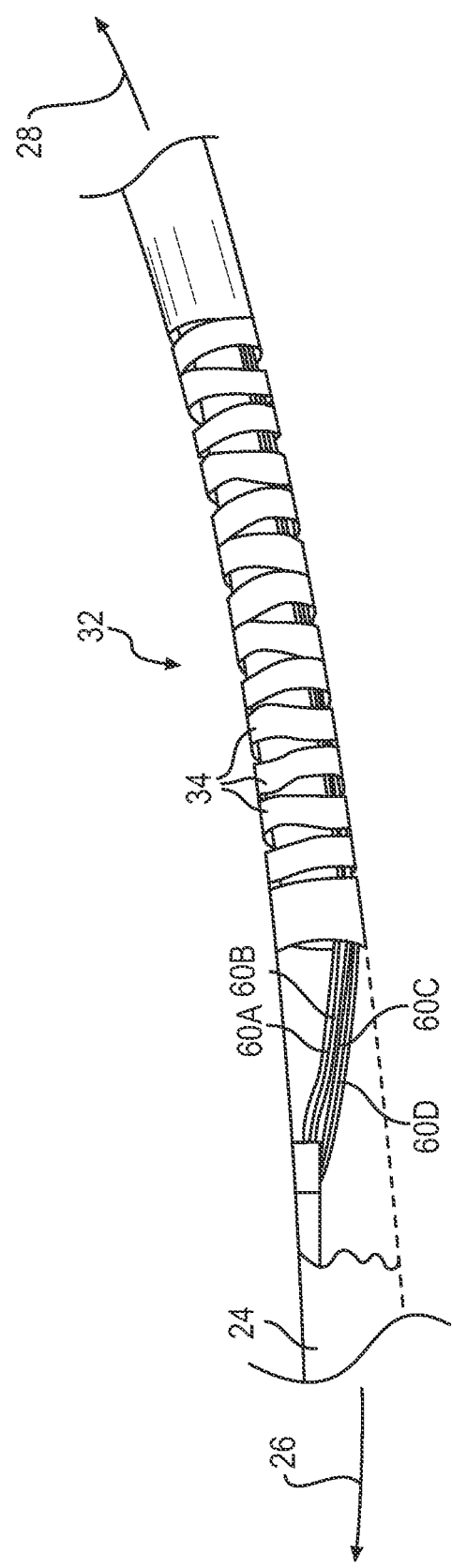
FIG. 2 illustrates an exemplary articulation portion of the catheter of FIG. 1.

FIG. 2 illustrates an exemplary articulation portion 32 of the guide tube 24. Articulation portion 32 includes segments 34 that are pivotably coupled together to form articulation joints that permit the segments 34 to move (such as, for example, at least partially rotate) with respect to each other. In some embodiments, the lumens of the guide tube 24 extend towards the distal end 28 through the inside of the segments 34. As the articulation portion 32 bends, the guide tube 24 along with the lumens bends. In some embodiments, some of the lumens extend through the inside of the segments 34 while others extend outside the segments 34. In some embodiments, a flexible covering (not shown), such as, for example, a mesh or a braid, may be provided over the articulation portion 32 to prevent the segments 34 from binding, pinching, and/or damaging the guide tube 24. A variety of control mechanisms may be used to manipulate the articulation portion 32 and flex the guide tube 24. In some embodiments, the control mechanism may include strings, wires, cable, or strands 60a, 60b, 60c, and 60d attached to one or more of the segments 34 to cause the segments 34 to move with respect to each other. When tensioned, these strands 60a, 60b, 60c, and 60d bend the articulation portion 32 in different directions by moving or rotating a series of segments 34. For example, in some embodiments, strands 60a and 60b may couple opposite sides of one or more segments 34 to the first dial 50a of the steering system 50. Rotating the first dial 50a may exert a pulling force or tension on one of the strands 60a, 60b and cause the segments 34 to bend the distal end 28 of the guide tube 24 up or down. The other strands 60c and 60d may similarly couple the segments 34 to the second dial 50b to bend the articulation portion 32 to the left and right. Articulation portion 32 may also include other features (not shown), such as, for example, springs, etc. that may assist in the deflection of guide tube 24. The articulation portion 32 and the segments 34 may include any suitable material. In some embodiments, the strands 60a, 60b, 60c, and 60d may be made of an elastic material, such as, for example, stainless steel. In some embodiments, the strands 60a, 60b, 60c, 60d include bowden cables with an outer sheath (made of a material such as PTFE) covering a lubricated inner filament.

Figure 3:
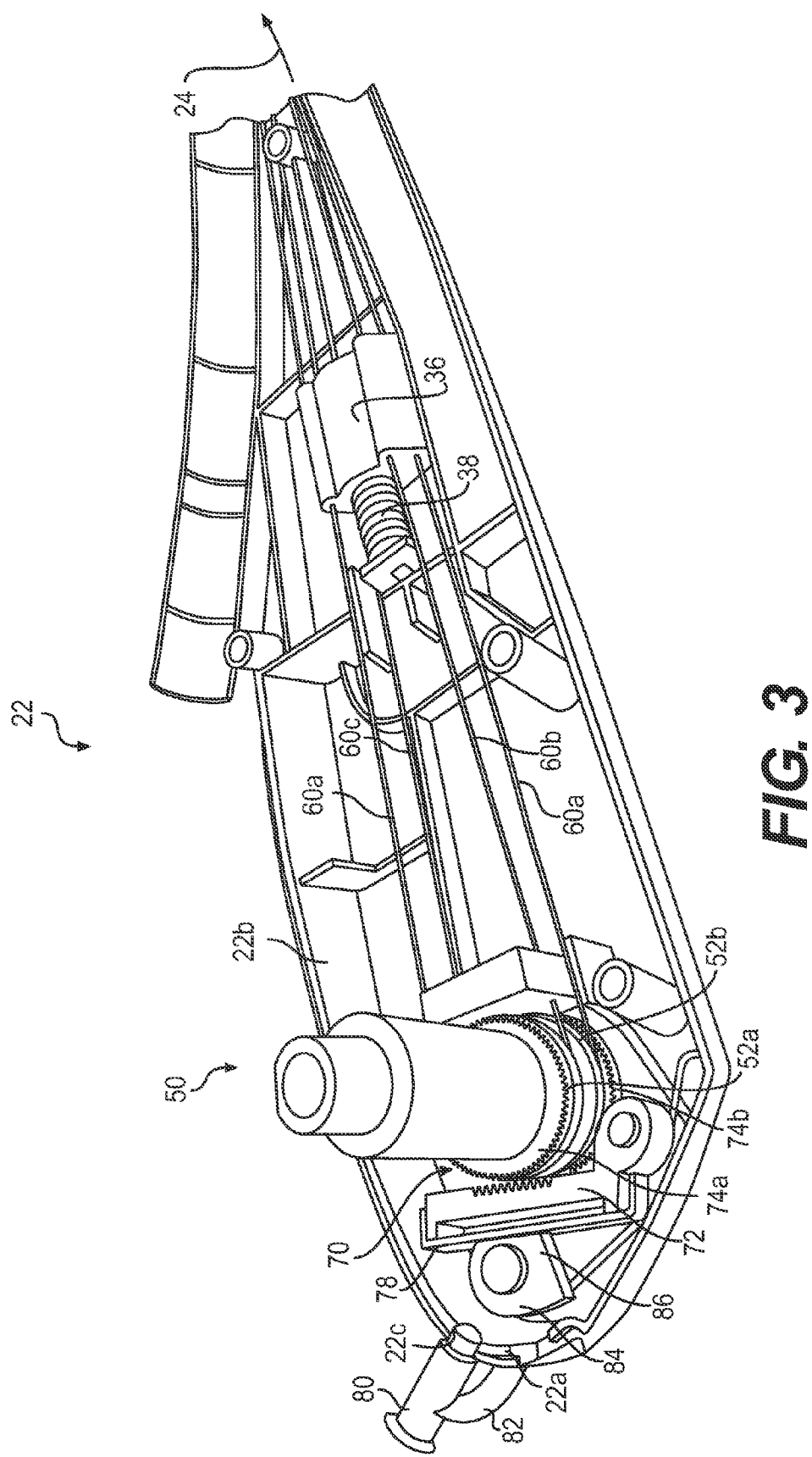
FIG. 3 illustrates inner portions of exemplary handle of the catheter of FIG. 1.

The handle 22 supports a portion of the steering system 50 that may be activated to deflect the guide tube 24 at the articulation portion 32. With reference to FIG. 1, handle 22 may include a body formed by two half sections 22a, 22b that may be joined together by any suitable method (such as, for example, using adhesives) to enclose a space therebetween. FIG. 3 is an illustration of an exemplary handle 22 with a half section 22a removed to show the structure within. Strands 60a, 60b, 60c, 60d that are coupled to articulation segments 34 may extend from the articulation portion 32 to the handle 22 through the guide tube 24. In some embodiments, these strands 60a, 60b, 60c, 60d may extend to the handle 22 through a lumen of the guide tube 24 and exit the lumen into the handle 22. In some embodiments, the strands may enter the handle 22 through a seal to prevent biological fluids from entering the handle 22. Within the handle 22, the strands 60a, 60b, 60c, 60d are coupled with the steering system 50 through a tensioner 36. In embodiments where the strands are bowden cables, the outer sheath of the bowden cables terminate at the tensioner 36, while the inner filament extends to the steering system 50. Tensioner 36 includes a spring 38 that keeps the filament taut between the tensioner 36 and the steering system 50, while allowing the portion of the cables distal to the tensioner 36 to flex and/or translate longitudinally.

Figure 4:
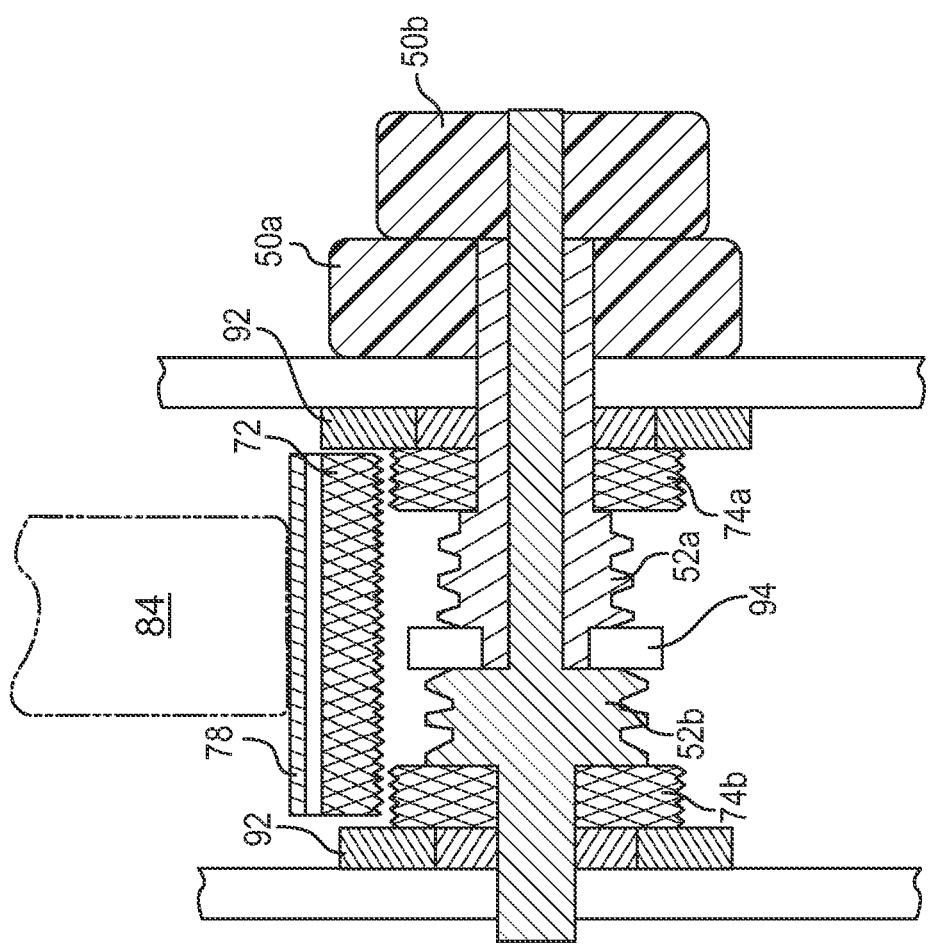
FIG. 4 illustrates a simplified cross-sectional view of portions of the handle of FIG. 3.

The strands 60a, 60b, 60c, 60d may be coupled to spools (first spool 52a and second spool 52b) of the steering system 50 that are connected to the first and second dials 50a, 50b. In some embodiments, two of the strands may be coupled to a first spool 52a and the other two strands may be coupled to a second spool 52b. For example, strands 60a and 60b may be coupled to opposite sides of the first spool 52a, and strands 60c and 60d may be coupled to the opposite sides of the second spool 52b. FIG. 4 illustrates a simplified cross-sectional view of portions of the exemplary handle 22 of FIG. 3 to illustrate the functioning of the steering system 50. In the description that follows, reference will be made to both FIGS. 3 and 4. The first spool 52a may be connected to the first dial 50a such that rotation of the first dial 50a rotates the first spool 52a and applies a pulling force to one of the strands 60a, 60b. As described previously, this pulling force causes the distal end 28 of the guide tube 24 to translate up or down at the articulation portion 32. Similarly, the second spool 52b may be connected to the second dial 50b such that rotation of the second dial 50b applies a pulling force on one of strands 60c and 60d and causes the guide tube 24 to move left or right. It should be noted that the number and configuration of strands and spools is only exemplary. The use of two spools and four strands allows independent articulation of the guide tube 24 in the left-right direction and the up-down direction. One skilled in the art will appreciate that the steering system 50 may alternatively be configured to control the up-down and left-right degrees of freedom of guide tube 24 in a different manner. In general, the number of strands and spools may depend on the number of degrees of freedom a catheter 20 is configured for. For example, in embodiments where the guide tube 24 is configured only to bend in one plane (for example, left and right), steering system 50 may include only a single spool and two strands.

Figure 5:
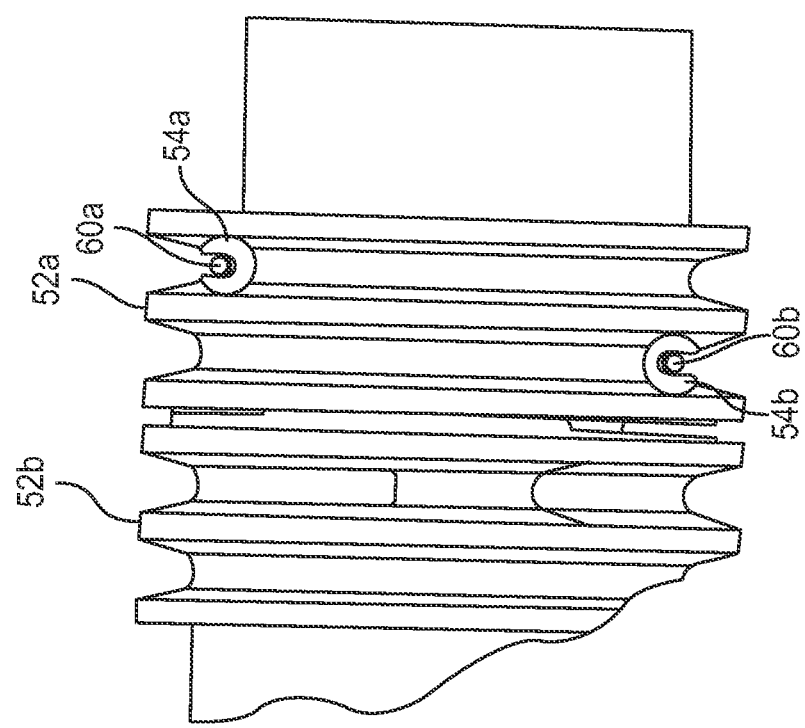
FIG. 5 illustrates an exemplary spool of the catheter of FIG. 1.

The strands 60a, 60b, 60c, 60d may be coupled to the spools 52a, 52b by any method. For example, in some embodiments, a strand may be fixedly attached to a spool by welding, adhering, etc. While in other embodiments, an end of a strand may be mechanically interlocked to a spool. FIG. 5 illustrates an exemplary embodiment of the spools (first spool 52a and second spool 52b) in which strands 60a and 60b are mechanically interlocked with the first spool 52a using retention tubes 54a, 54b. In some embodiments, a terminal at the end of a strand (for example, strand 60a) may pass through a slot of a retention tube (for example, retention tube 54a) to mechanically interlock the strand with the spool. The retention tubes 54a, 54b may be tangential pockets or other features machined into the first spool 52a or may be a separate component attached to the first spool 52a. In some embodiments, the retention tubes 54a, 54b may be comprised of an annealed stainless steel or another material to allow for controlled deformation of the tubes while prophylactically preventing damage to the strands.

Figure 7B:
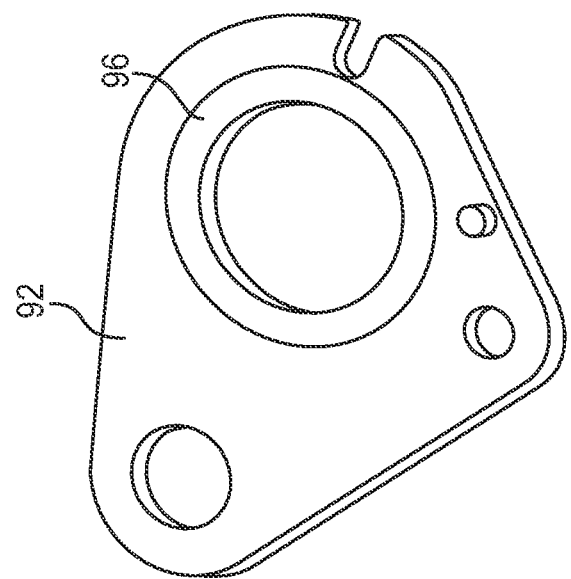
FIG. 7B illustrates an exemplary brake bracket of the catheter of FIG. 1.
Figure 7A:
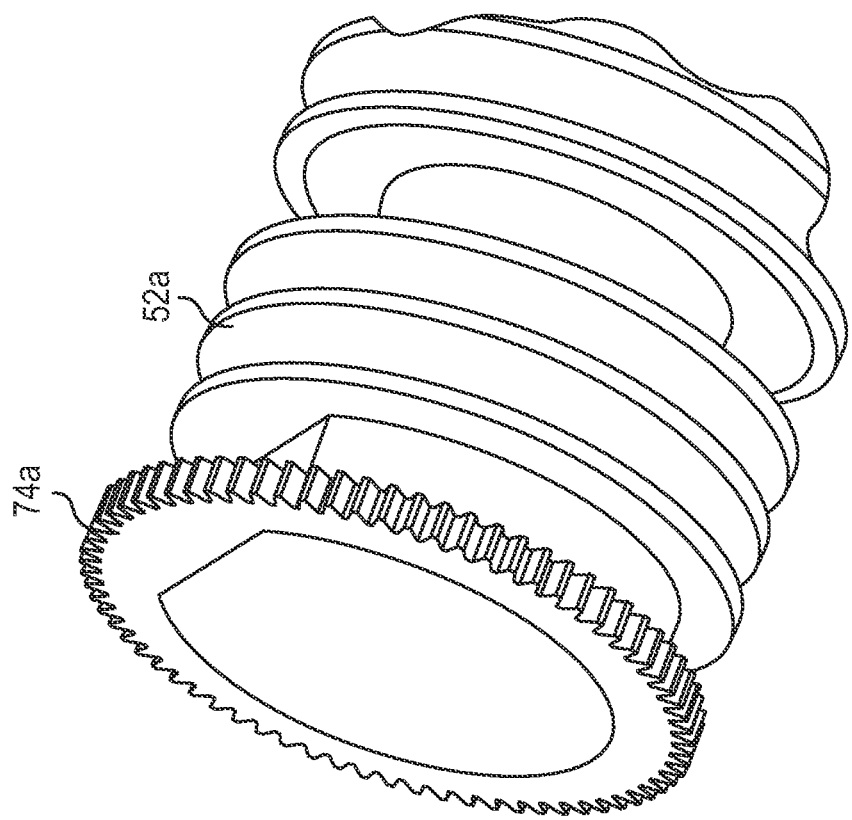
FIG. 7A illustrates an exemplary arrangement of a pinion and a spool of the catheter of FIG. 1.

Steering system 50 may also include a brake mechanism 70 configured to lock the guide tube 24 in position once a desired configuration of articulation portion 32 is reached (see FIGS. 3 and 4). When engaged, the brake mechanism 70 provides a positive lock for the guide tube 24 (and particularly the articulation portion 32) and prevents inadvertent movement of the guide tube 24. FIGS. 6A and 6B illustrate portions of the steering system 50 showing an exemplary brake mechanism 70 of catheter 20. With reference to FIGS. 3, 4, 6A and 6B, in one embodiment, the brake mechanism 70 includes a rack gear or a shoe 72 and pinion gears or pinions (first pinion 74a and second pinion 74b). First pinion 74a may be coupled with the first spool 52a such that relative movement (or relative rotation) between the first spool 52a and the first pinion 74a is prevented. That is, the first spool 52a and the first pinion 74a may be fixedly coupled together and rotate as one part. Similarly, the second pinion 74b and the second spool 52b may be coupled together such that relative movement between them is prevented. In some embodiments, a geometry of a pinion (for example, first pinion 74a) and a spool (for example, first spool 52a) may ensure that relative movement between the pinion and the spool is prevented. FIG. 7A illustrates an exemplary geometry of first pinion 74a and first spool 52a that may be applied in brake mechanism 70. As illustrated in FIG. 7A, the first spool 52a may include a spindle with a flat region on its circumference that may mate with a corresponding region of the first pinion 74a to prevent relative movement between them. It should be noted that the configuration illustrated in FIG. 7A is only exemplary, and relative movement between a pinion and a spool may be prevented by any method. For example, in some embodiments, a corresponding pinion and a spool may be attached using adhesives. It is also contemplated that in some embodiments, a corresponding pinion and a spool may be fabricated as one part.

Engagement of the brake mechanism 70 forces the shoe 72 to mate with the first and second pinions 74a and 74b and prevent the rotation of the spools 52a, 52b. In some embodiments, the shoe 72 may be spring loaded such that the shoe 72 separates from the first and second pinions 74a and 74b and returns to a neutral position when the brake mechanism 70 is disengaged. In some embodiments, the shoe 72 may be spring loaded by a torsion spring 76 (see FIGS. 6A, 6B) that biases the shoe in a direction away from the pinions. In some embodiments, shoe 72 may be straight (as shown in FIGS. 6A and 6B), curved, or other shapes. It is contemplated that in certain embodiments, engagement of a single tooth of shoe 72 and first or second pinions 74a and 74b is sufficient to lock first and second spools 52a and 52b. It is also contemplated gear teeth may extend along the full length of shoe 72 or may extend along a partial length of shoe 72. For example, shoe 72 may have teeth that only extend along the portion or portions of shoe 72 that are configured to engage pinions 74a and 74b.

With reference to FIGS. 6A and 6B, the brake mechanism 70 may be engaged by pulling a spring loaded brake lever 80 upwards in the direction of arrow B and rotating the brake lever 80 from a first position to a second position in the direction of arrow A. The brake lever 80 may be biased towards the handle 22 (that is, in a direction opposite arrow B) by a spring or by another mechanism. The handle 22 may lock into a slot in the handle 22 or may include a feature to retain (or lock) the brake lever 80 and prevent its rotation (along arrow A) when the brake lever 80 is engaged with this feature. Any type of feature may be used to retain the brake lever 80 in the handle 22. In some embodiments, the body of the handle 22 may include an opening to retain a distal end of the brake lever 80 and prevent its rotation. In some embodiments, the handle 22 may include a first opening 22c at the first position and a second opening 22d at the second position to retain the brake lever 80 at these two positions. Pulling the brake lever 80 in the direction of arrow B may pull the distal end of the lever 80 out of the first opening 22c and allow the lever 22 to rotate towards the second position in the direction of arrow A. At the second position, the distal end of the brake lever 80 may enter, and thereby be retained by, the second opening 22d. In some embodiments, the handle 22 may include only one opening at either the first position or second position to lock the brake lever 80 at that position. Although openings in the handle 22 are described as the brake lever retention features, this is only exemplary. Any type of feature (such as, for example, a projection in the handle 22) may be used as a retention feature. The spring which biases the brake lever 80 towards the handle 22 may be internal or external. The engagement of the brake lever 80 with features (such as, the first and second openings 22c, 22d) in the handle 22 serves as in integral safety interlock that prevents inadvertent activation or deactivation of the brake mechanism 70.

The brake lever 80 may be coupled through arms 82 to a cam 84 positioned within the handle 22. The cam 84 may include a lobe 86 shaped to push the shoe 72 towards the pinions 74a, 74b, and thereby cause the gears of the shoe 72 to engage with the gears of the pinions 74a, 74b, when the brake lever 80 rotates from the first position to the second position. Releasing the lever 80 at the second position may force the distal end of the spring loaded brake lever 80 into the second opening 22d and thereby prevent accidental rotation of the lever 80 towards the first position. Activation (and, in some embodiments, deactivation) of the brake mechanism 70 requires two deliberate movements of the brake lever 80 (pulling the brake lever 80 in the direction of arrow B, and rotating the brake lever 80 in the direction of arrow A) to prevent inadvertent activation of the brake mechanism 70.

In some embodiments, a compliant leaf spring 78 may be provided between the cam 84 and the shoe 72 to limit the need for tight tolerance between the components of the brake mechanism 70. Deformation of the leaf spring 78 accommodates variations in dimensions of different parts of the brake mechanism 70, and limits the force needed to engage the brake mechanism 70. In some embodiments, brake brackets 92 (see FIGS. 6A, 6B) may be provided between the pinions 74a, 74b and the body of the handle 22 to allow for easy rotation of the spools 52a, 52b. FIG. 7B illustrates an exemplary brake bracket 92 that may be used in the brake mechanism 70. The brake bracket 92 may include an integral bearing 96 to provide lubricity and alignment of the spools 52a, 52b with the pinions 74a, 74b. The brake bracket 92 may also provide torsional rigidity to the brake mechanism 70. It should be noted that the structure of the brake mechanism components described herein is only exemplary, and several modifications may be made to these components. For example, in some embodiments, a pinion may be incorporated with a corresponding spool (that is, the first spool 52a may be integral with the first pinion 74a, and the second spool 52b may be integral with the second pinion 74b), and the leaf spring 78 may be incorporated with the shoe 72.

In the embodiment of brake mechanism 70 described above, the shoe 72 engages with both the first pinion 74a and the second pinion 74b when the brake mechanism 70 is activated (i.e., by moving brake lever 80 to opening 22d). However, this is only exemplary. In some embodiments, the shoe 72 may engage with only one of the pinions during activation of the brake mechanism 70. In such embodiments, activation of a first brake mechanism 70 may lock the movement of the guide tube 24 in one direction (for example, up-down), and activation of a second brake mechanism may lock the movement of the guide tube 24 in another direction (for example, left-right). It is also contemplated that, in some embodiments, the shoe 72 may engage with the two pinions in stages. For example, the shoe 72 may first engage with the first pinion 74a when the brake lever 80 is rotated to the second position, and then engage with the second pinion 74b when the lever 80 is further rotated to a third position. Although the shoe 72 and the pinions 74a, 74b are described as including gears, this is only exemplary. In some embodiments, the gears may be replaced with other features (such as a pad of material with a relatively high coefficient of friction) that prevents or minimizes relative movement between the shoe and a pinion. It is contemplated that, in some embodiments, brake 70 may alternatively include a strap or cable or other tensioning device configured to surround and spools 52a and 52b and resist or prohibit rotation of the spools when tightened. For example, a strap or cable may be formed from relatively high friction material and tightened against portions of hubs 52a and 52b upon actuation of the brake lever 80. It is also contemplated that some embodiments shoe 72 and pinions 74a and 74b may comprise materials of relatively high friction or may elastically deform to improve braking. It is contemplated that any number of control wheels 50a and 50b as well as any number of hubs 52a and 52b may be included. For example, control wheels may be stacked one on another on a single side of the handle 22 or positioned one on each side of handle 22. In addition, it is contemplated that multiple sets of stacked control wheels may be positioned on a single side of handle 22. In some embodiments, the stacked control wheels could control different deflection of a single articulation point. In other embodiments one set of control wheels could control a first articulation point and a second set of control wheels could control a second articulation point. In such embodiments, it is contemplated that a single brake lever could control all sets of stacked control wheels or multiple brake levers could be implemented to independently control sets of stacked control wheels. It is further contemplated that control wheels configured to control a single articulation point may be on different portions of handle 22.

Figure 8:
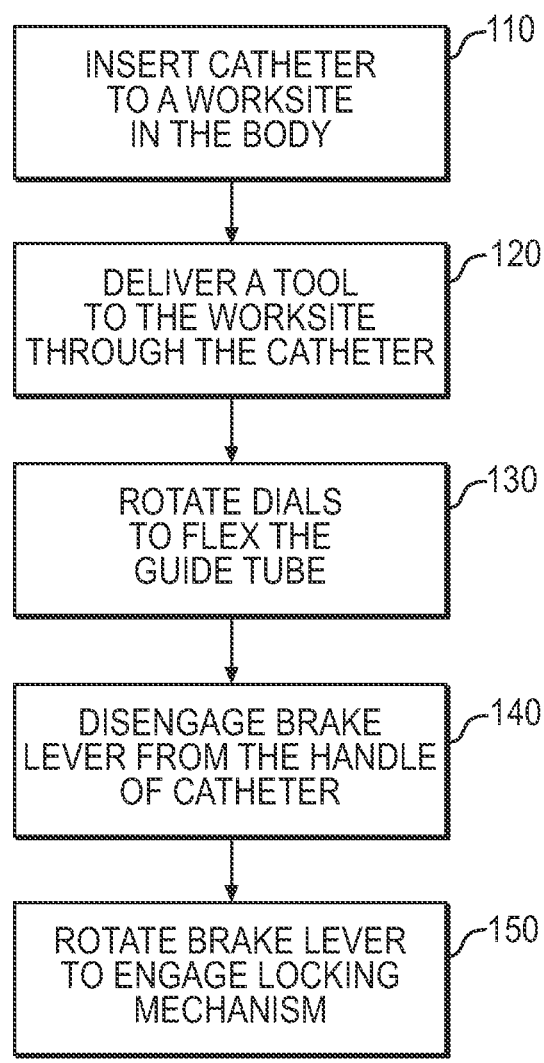
FIG. 8 illustrates an exemplary method of using the steerable catheter of FIG. 1.

FIG. 8 is a flow chart that illustrates a method of using a catheter 20 including a brake mechanism 70. In the description below, reference will be made to both FIGS. 1, 3 and 8. The distal end 28 of the guide tube 24 of the catheter 20 may be inserted into a body and pushed in until the distal end 28 is positioned at a work site within the body (step 110). One or more surgical or therapeutic tools may be delivered to the work site through the lumens of the guide tube 24 (step 120). Dials 50*a* and 50*b* of the steering system 50 may be to the rotated to flex the articulation portion 32 of the guide tube 24, and thereby suitably position the distal end 28 of the guide tube 24 at the work site (step 130). When the distal end 28 is suitably positioned, the brake lever 80 may be first disengaged from the retention feature in handle 22 (that is, pulled out of opening 22*c*) (step 140), and then rotated (in the direction of arrow A) to engage the brake mechanism 70 (step 150). Engagement of the brake mechanism 70 locks the position of the dials 50*a*, 50*b*, and thereby freezes the configuration of the guide tube 24 (particularly the articulation portion 32) to prevent inadvertent movement of its distal end 28. Since activation and/or deactivation of the locking mechanism 70 requires two deliberate movements of the brake lever 80, accidental activation or deactivation can be avoided.

The embodiments described herein are exemplary only, and it will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims.

What is claimed is:

1. A catheter, comprising:
   a handle;
   a tubular member extending from the handle;
   a steering system coupled to the handle, the steering system being configured to deflect at least a portion of the tubular member in at least one direction;
   a locking mechanism configured to lock the portion of the tubular member in a deflected configuration, wherein the locking mechanism comprises:
      a rack gear and at least one pinion gear;
      a cam that rotates to push the rack gear towards the at least one pinion gear; and
      a leaf spring configured to act as an interface between the cam and the rack gear; and
   a lever coupled to the handle and configured to move from a first position to a second position to engage the locking mechanism by rotating the cam to push the rack gear towards the at least one pinion gear when the lever is moved from the first position to the second position, wherein the lever is configured to be separably retained at least at one of the first position or the second position to prevent movement therebetween.

2. The catheter of claim 1, wherein the rack gear and the pinion gear are each toothed gears.

3. The catheter of claim 1, wherein the steering system includes at least one spool that is configured to rotate to deflect the portion of the tubular member, the at least one pinion gear being coupled to the at least one spool such that relative rotation between them is prevented.

4. The catheter of claim 1, wherein movement of the lever from the first position to the second position causes the rack gear to mate with the at least one pinion gear.

5. The catheter of claim 1, wherein the steering system includes two spools, each spool being configured to deflect the portion of the tubular member in a different direction, wherein the rack gear prevents the rotation of both spools when the locking mechanism is engaged by the lever.

6. The catheter of claim 1, wherein the locking mechanism includes a spring configured to bias the rack gear in a direction away from the at least one pinion gear.

7. The catheter of claim 1, wherein the locking mechanism includes a spring configured to bias the lever towards the handle, and the handle includes a retention feature configured to retain the lever at least at one of the first position or the second position.

8. The catheter of claim 7, wherein the retention feature is an opening in the handle, and the lever is separably retained by the handle by accommodating a distal end of the lever in the opening.

9. The catheter of claim 1, wherein the lever is configured to be pulled in a direction away from the handle and pivot relative to the handle to move from the first position to the second position.

10. A catheter, comprising:
    a handle;
    a tubular member extending from the handle;
    a steering system coupled to the handle, the steering system including:
       at least one spool configured to rotate to deflect at least a portion of the tubular member in at least one direction; and
    a locking mechanism configured to interact with the steering system to lock the portion of the tubular member in a deflected configuration, wherein the locking mechanism comprises:
       a pinion gear fixedly coupled to the at least one spool;
       a rack gear configured to engage with the pinion gear to lock the portion of the tubular member in the deflected configuration when the locking mechanism is engaged;
       a cam that is rotatable to push the rack gear towards the pinion gear; and
       a leaf spring configured to act as an interface between the cam and the rack gear; and
    a lever coupled to the handle and configured to move from a first position to a second position to engage the locking mechanism by rotating the cam to push the rack gear towards the pinion gear when the lever is moved from the first position to the second position, wherein the lever is configured to be separably retained at least at one of the first position or the second position to prevent movement therebetween.

11. The catheter of claim 10, wherein the lever includes a releasable lock that is configured to prevent movement of the lever between the first position and the second position.

12. The catheter of claim 11, wherein the releasable lock includes a spring that biases the lever towards a retention feature on the handle.

13. The catheter of claim 11, wherein the steering system includes two spools, each spool being fixedly coupled to a pinion gear, wherein each spool is configured to deflect the portion of the tubular member in a different direction.

14. A method of using a catheter including a handle with a tubular member extending therefrom, the method comprising:
- positioning the catheter in a body with a distal end of the tubular member within the body and the handle outside the body;
- activating a steering mechanism coupled to the handle to deflect at least a portion of the tubular member in at least one direction; and
- engaging a locking mechanism of the catheter to lock the portion of the tubular member in a deflected configuration, wherein the engaging includes:
  - unlocking a lever coupled to the handle; and
  - moving the lever from a first position to a second position to engage the locking mechanism, wherein the lever is configured to be separably retained at least at one of the first position or the second position to prevent movement therebetween,
- wherein moving the lever from the first position to the second position rotates a cam to push a rack gear towards a pinion gear so that the rack gear mates with the pinion gear, and wherein a leaf spring acts as an interface between the cam and the rack gear.

15. The method of claim 11, wherein the pinion gear is fixedly coupled to a spool of the catheter.

16. The catheter of claim 10, wherein the steering system further includes:
- at least one strand coupled to the at least one spool; and
- at least one dial coupled to the at least one spool, wherein the at least one spool is configured to rotate in response to rotation of the at least one dial to exert a force on the at least one strand to deflect at least a portion of the tubular member in at least one direction.

* * * * *